United States Patent [19]

Applegate et al.

[11] 4,293,420

[45] Oct. 6, 1981

[54] TREATMENT OF REVERSE OSMOSIS MEMBRANES

[75] Inventors: Lynn E. Applegate, Wilmington; Charles J. Brown, Jr., Hockessin, both of Del.

[73] Assignee: E. I. Du Pont de Nemours and Company, Wilmington, Del.

[21] Appl. No.: 141,661

[22] Filed: Apr. 18, 1980

[51] Int. Cl.³ .............................................. B01D 13/00
[52] U.S. Cl. .................................................. 210/500.2
[58] Field of Search ........................... 210/500.2, 321.2; 264/41, 216, 340

[56] References Cited

U.S. PATENT DOCUMENTS

| | | | |
|---|---|---|---|
| 3,423,491 | 1/1969 | McLain et al. | 210/500.2 |
| 3,551,331 | 12/1970 | Cescon et al. | 210/500.2 |
| 3,567,632 | 3/1971 | Richter et al. | 210/654 |

*Primary Examiner*—Charles N. Hart
*Assistant Examiner*—E. Rollins Cross

[57] ABSTRACT

Process for the treatment of Reverse Osmosis membranes to extend their storage life when immersed in water by the addition of magnesium calcium or sodium ions to the water.

6 Claims, No Drawings

TREATMENT OF REVERSE OSMOSIS MEMBRANES

BACKGROUND OF THE INVENTION

Semipermeable membranes have long been used for the purification of water. Such membranes are useful, for example, in the removal of dissolved inorganic salts. In such processes, water containing the dissolved salts is held under pressure against a membrane which passes water but does not pass the salt ions.

Polyamide reverse osmosis membranes have been used in the form of hollow filaments or flat films in cartridges for the purification of saline and brackish waters. It is often necessary, however, to store the reverse osmosis membranes for extended periods before they are put into use, either due to extended periods for transportation or inventory requirements. The membranes are normally stored in a wet condition, and the water used for storage frequently contains additives which decrease the pH of the aqueous solution. For example, bacteriostats such as formaldehyde are typically added in concentrations of about from 5 parts per million to 1 percent by weight to inhibit the growth of bacteria during storage. The formaldehyde, however, degrades to formic acid, which results in the decrease in pH of the storage solution. With increasing degrees of acidity, the polyamide membranes tend to degrade, thus reducing their performance capabilities and effective life.

SUMMARY OF THE INVENTION

The instant invention provides an improved process for the storing of polyamide reverse osmosis membrane which permits extended storage of the membranes in an aqueous medium having a low pH.

Specifically, the instant invention provides, in a process for storing polyamide reverse osmosis membrane by immersing the membrane in an aqueous medium, the improvement which comprises adding to the aqueous medium a metal ion selected from the group consisting of about $8 \times 10^{-4}$ to $8 \times 10^{-2}$ moles per liter of at least one alkaline earth metal ion, and about from $8 \times 10^{-3}$ to $4 \times 10^{-1}$ moles per liter of at least one alkali metal ion.

DETAILED DESCRIPTION OF THE INVENTION

The present invention is applicable to a wide variety of polyamide reverse osmosis membranes. However, particularly satisfactory are those aromatic, nitrogen-containing polymeric membranes described in Richter et al. U.S. Pat. No. 3,567,632, hereby incorporated by reference. The membrane can be in any convenient form, including flat membranes as well as hollow fibers spun from the polyamide. Typically, a reverse osmosis cartridge containing many individual permselective hollow fiber membranes is prepared and shipped in a water-wet state for installation in a reverse osmosis apparatus. The aqueous medium used for storage generally has an initial pH from about from 4 to 11, and contains about from 5 parts per million to 1 percent by weight of a bacteriostat, most typically formaldehyde. The degradation of the formaldehyde to formic acid frequently increases the acidity of the aqueous storage medium to a pH of 4 or below.

The process of the present invention involves the addition of alkali or alkaline earth metal ions to the aqueous storage solution. While ions of any of the alkali or alkaline earth metals can be used in the present invention, several are preferred because of low cost and ready availability. These include lithium, sodium and potassium of the alkali metals and magnesium and calcium of the alkaline earth metals.

The ions can be added in the form of any salt which exhibits satisfactory water solubility. Thus, salts which can be used to add the metal ions to the solution include magnesium, calcium or sodium chlorides, sodium or magnesium sulfates, magnesium or sodium carbonates or bicarbonates, and magnesium, calcium or sodium nitrates. Particularly preferred for use in the instant invention are the magnesium chlorides or nitrates. The alkaline earth metal ions are used in concentrations of about from $8 \times 10^{-4}$ to $8 \times 10^{-2}$ moles per liter. Less than $8 \times 10^{-4}$ moles per liter result in little beneficial affect on the stability of the reverse osmosis membranes, while little added benefit is obtained in concentrations of the alkaline earth metal ion in excess of $8 \times 10^{-2}$ moles per liter. Concentrations of about from $8 \times 10^{-3}$ to $2 \times 10^{-2}$ moles per liter of the alkaline earth metal ions are particularly preferred.

The quantities of alkali metal ion needed to realize the benefits of the present invention are somewhat higher, and about from $8 \times 10^{-3}$ to $4 \times 10^{-1}$ moles per liter should be used, and preferreably about from $4 \times 10^{-2}$ to $8 \times 10^{-2}$ moles per liter. Concentrations of alkali metal ion in excess of $4 \times 10^{-1}$ moles per liter can result in the possible osmotic degradation of the polyamide reverse osmosis membrane.

The addition of the metal ions in accordance with the present invention results in a marked increase in the stability of the reverse osmosis membranes in aqueous media with a pH as low as 2.5. Thus, it is possible to enjoy the benefits of bacteriostat in an aqueous storage medium and avoid degradation of the polyamide reverse osmosis membrane at the same time.

The invention is further illustrated in the following specific examples, in which parts and percentages are by weight unless otherwise indicated. In these examples, reverse osmosis fibers are tested by storing in an aqueous solution having a pH of 2.5.

After various intervals, the degree of degradation of the fibers was measured by testing the fiber tensile elongation. A reduction in fiber tensile elongation of 95% or more is considered to represent complete degradation of the fiber.

EXAMPLES 1 AND 2 AND COMPARATIVE EXAMPLES A AND B

In these Examples, aromatic polyamide hollow fibers were prepared according to Richter et al., U.S. Pat. No. 3,567,632, Example 1-V, except that the ratio of the meta-phenylene diamine/calcium-sulfonated meta-phenylene diamine is 80/20 instead of 88.5/11.5. The fibers were stored in aqueous solutions having the ion concentration indicated in Table I.

TABLE I

| Ex. | Ion | Concentration (moles/liter) |
|---|---|---|
| 1 | $Mg^{++}$ | $8.7 \times 10^{-4}$ |
| 2 | $Ca^{++}$ | $8.7 \times 10^{-4}$ |
| A | — | — |
| B | $Na^+$ | $8.7 \times 10^{-4}$ |

After storage, the fibers in Comparative Examples A and B were completely degraded in eight weeks. The fibers in Examples 1 and 2 required 16 weeks storage to degrade to the same degree.

EXAMPLES 3, 4, and 5

The procedure of Example 1 was repeated, using the ion concentrations shown in Table II.

TABLE II

| Ex. | Ion | Concentration (moles/liter) |
|---|---|---|
| 3 | $Mg^{++}$ | $8.7 \times 10^{-3}$ |
| 4 | $Ca^{++}$ | $8.7 \times 10^{-3}$ |
| 5 | $Na^+$ | $8.7 \times 10^{-3}$ |

The fibers in Comparative Example 5 exhibited complete degradation after 16 weeks, while the fibers in Examples 3 and 4 retained 80% of their fiber tensile elongation after this period of storage.

EXAMPLES 6–8

The procedure of Example was repeated, using the ion concentrations indicated in Table II.

TABLE III

| Ex. | Ion. | Concentration (moles/liter) |
|---|---|---|
| 6 | $Na^+$ | $4.4 \times 10^{-2}$ |
| 7 | $Mg^{++}$ | $4.4 \times 10^{-2}$ |
| 8 | $Ca^{++}$ | $4.4 \times 10^{-2}$ |

The fibers in Example 6 lost 50% of their initial fiber tensile elongation after 16 weeks. The fibers in Examples 7 and 8 retained 85% or more of their initial fiber tensile elongation after the same period of storage.

EXAMPLES 9 AND 10 AND COMPARATIVE EXAMPLES C AND D

The general procedure of Examples 1 to 2 and Comparative Examples A and B was repeated, using a different aromatic polyamide fiber, prepared as described in Richter et al., U.S. Pat. No. 3,567,632, Example 1-V. The fibers were stored and tested as before, using the concentrations of ions indicated in Table IV.

TABLE IV

| Ex. | Ion | Concentration (moles/liter) |
|---|---|---|
| 9 | $Mg^{++}$ | $8.7 \times 10^{-4}$ |
| 10 | $Ca^{++}$ | $8.7 \times 10^{-4}$ |
| C | — | — |
| D | $Na^+$ | $8.7 \times 10^{-4}$ |

The fibers in Comparative Examples C and D suffered complete degradation after 4 weeks. The fibers in Examples 9 and 10 required 8 weeks to degrade.

EXAMPLES 11 AND 12 AND COMPARATIVE EXAMPLE E

The general procedure for Examples 9 and 10 was repeated, using the ions in concentrations indicated in Table V.

TABLE V

| Ex. | Ion | Concentration (moles/liter) |
|---|---|---|
| 11 | $Mg^{++}$ | $8.7 \times 10^{-3}$ |
| 12 | $Ca^{++}$ | $8.7 \times 10^{-3}$ |
| E | $Na^+$ | $8.7 \times 10^{-3}$ |

The fibers were tested as previously described. The fibers from Comparative Example E degraded in 8 weeks. The fibers from Examples 11 and 12 retained more than 60% of their original fiber tensile elongation after 16 weeks of storage.

EXAMPLES 13 TO 15

The general procedure of Examples 8 and 9 was repeated, using the ion concentrations indicated in Table VI.

TABLE VI

| Ex. | Ion | Concentration (moles/liter) |
|---|---|---|
| 13 | $Na^+$ | $4.4 \times 10^{-2}$ |
| 14 | $Mg^{++}$ | $4.4 \times 10^{-2}$ |
| 15 | $Ca^{++}$ | $4.4 \times 10^{-2}$ |

The fibers of Example 13 retained approximately 35% of their original tensile elongation after 16 weeks of storage. The fibers from Examples 14 and 15 retained greater than 75% of their original tensile elongation values after the same periof of storage.

We claim:

1. In the process for storing polyamide reverse osmosis membranes by immersing the membrane in an aqueous medium, the improvement which comprises adding to the aqueous medium at least one metal ion selected from the group consisting of about from $8 \times 10^{-4}$ to $8 \times 10^{-2}$ moles per liter of an alkaline earth metal ion and about from $8 \times 10^{-3}$ to $4 \times 10^{-1}$ moles per liter of an alkali metal ion.

2. A process of claim 1 wherein the metal ion is an alkaline earth metal ion selected from magnesium or calcium 3. A process of claim 2 wherein the ion is present in a concentration of about from $8 \times 10^{-3}$ to $2 \times 10^{-2}$ moles per liter.

4. A process of claim 1 wherein the metal ion is sodium.

5. A process of claim 4 wherein the sodium ion is present in an amount of about from $4 \times 10^{-2}$ to $8 \times 10^{-2}$ moles per liter.

6. A process of claim 1 wherein the ion is added in the form of a chloride or nitrate salt.

* * * * *